(12) United States Patent
Glasgow et al.

(10) Patent No.: US 12,046,328 B2
(45) Date of Patent: Jul. 23, 2024

(54) METHOD, NON-TRANSITORY COMPUTER-READABLE MEDIA, AND SYSTEM FOR E-COMMERCE REPLACEMENT OR REPLENISHMENT OF CONSUMABLE

(71) Applicant: eBay Inc., San Jose, CA (US)

(72) Inventors: Dane Glasgow, Los Altos, CA (US); Matthew Brett MacLaurin, Santa Cruz, CA (US); David Ramadge, San Jose, CA (US); Corinne Elizabeth Sherman, San Jose, CA (US)

(73) Assignee: EBAY INC., San Jose, CA (US)

( * ) Notice: Subject to any disclaimer, the term of this patent is extended or adjusted under 35 U.S.C. 154(b) by 0 days.

(21) Appl. No.: 18/055,469

(22) Filed: Nov. 15, 2022

(65) Prior Publication Data
US 2023/0075002 A1 Mar. 9, 2023

Related U.S. Application Data

(63) Continuation of application No. 16/590,362, filed on Oct. 1, 2019, now Pat. No. 11,556,971, which is a
(Continued)

(51) Int. Cl.
*G06Q 30/00* (2023.01)
*G06F 16/23* (2019.01)
(Continued)

(52) U.S. Cl.
CPC ......... *G16B 30/20* (2019.02); *G06F 16/2365* (2019.01); *G16B 30/10* (2019.02)

(58) Field of Classification Search
None
See application file for complete search history.

(56) References Cited

U.S. PATENT DOCUMENTS

| 4,052,882 A | 10/1977 | Wittkowski |
| 4,799,169 A | 1/1989 | Mims |

(Continued)

FOREIGN PATENT DOCUMENTS

| AU | 2014364486 | 5/2017 |
| CA | 2929957 | 5/2015 |

(Continued)

OTHER PUBLICATIONS

Hsu, C.F., Smart Pantries for Homes, Oct. 1, 2006, 2006 IEEE International Conference on Systems, Man, and Cybernetics, vol. 5, pp. 4276-4283 (Year: 2006).*

(Continued)

*Primary Examiner* — Allison G Wood
*Assistant Examiner* — Timothy J Kang
(74) *Attorney, Agent, or Firm* — SCHWEGMAN LUNDBERG & WOESSNER, P.A.

(57) ABSTRACT

Methods and systems for replenishing a consumable include order satisfaction responsive to an indication of imminent failure or depletion of a consumable based on detected parameters. A sensor reading may indicate that a consumable is performing below a threshold, or has limited remaining capacity. Responsive to a determination that a replacement is necessary, the method may recommend one or more alternatives. The recommendation may be made based on how closely a candidate replacement's performance or other characteristic (e.g. cost, capacity) matches that of a currently-used consumable. The recommendation may be based on one or more attributes of a candidate replacement compared to a currently-used consumable. An order may be automatically placed according to the currently-used consumable or the recommended alternative(s). The order may be delivered with instructions regarding where and when to replace the consumable.

20 Claims, 6 Drawing Sheets

Related U.S. Application Data continuation of application No. 14/588,320, filed on Dec. 31, 2014, now Pat. No. 10,430,858.

(51) Int. Cl.
*G16B 30/10* (2019.01)
*G16B 30/20* (2019.01)

(56) References Cited

U.S. PATENT DOCUMENTS

| | | | |
|---|---|---|---|
| 4,846,701 A | 7/1989 | Hayes et al. | |
| 4,947,028 A | 8/1990 | Gorog | |
| 5,168,445 A | 12/1992 | Kawashima et al. | |
| 5,568,539 A | 10/1996 | Bergsman et al. | |
| 5,642,197 A | 6/1997 | Tuhro et al. | |
| 5,952,832 A | 9/1999 | Stevanovic et al. | |
| 6,341,271 B1 | 1/2002 | Salvo et al. | |
| 6,362,573 B1 | 3/2002 | Helbing et al. | |
| 6,751,525 B1 | 6/2004 | Crisp, III | |
| 6,853,291 B1 | 2/2005 | Aisa | |
| 7,010,502 B1 | 3/2006 | Hoshizawa et al. | |
| 7,130,814 B1 | 10/2006 | Szabo et al. | |
| 7,426,490 B1 | 9/2008 | Borsand et al. | |
| 7,729,951 B2 | 6/2010 | Dawson et al. | |
| 8,498,888 B1 | 7/2013 | Raff et al. | |
| 8,538,829 B1* | 9/2013 | Hu | G06Q 30/0631 |
| | | | 705/26.1 |
| 8,924,262 B2* | 12/2014 | Shuster | G06Q 30/0601 |
| | | | 705/28 |
| 9,306,828 B2 | 4/2016 | Fahimi et al. | |
| 9,324,042 B2 | 4/2016 | Agarwal | |
| 9,449,208 B2 | 9/2016 | Luk et al. | |
| 9,829,887 B2 | 11/2017 | Zhu et al. | |
| 10,430,858 B1 | 10/2019 | Glasgow et al. | |
| 10,508,968 B1 | 12/2019 | Vaganay et al. | |
| 10,593,199 B1 | 3/2020 | Slusar | |
| 11,030,571 B2 | 6/2021 | Glasgow et al. | |
| 11,107,023 B2 | 8/2021 | Glasgow et al. | |
| 11,556,971 B2 | 1/2023 | Glasgow et al. | |
| 11,836,673 B2 | 12/2023 | Glasgow et al. | |
| 11,853,944 B2 | 12/2023 | Glasgow et al. | |
| 2001/0014868 A1 | 8/2001 | Herz et al. | |
| 2001/0017023 A1 | 8/2001 | Armington et al. | |
| 2002/0091592 A1 | 7/2002 | Sugiura et al. | |
| 2002/0161652 A1 | 10/2002 | Paullin et al. | |
| 2002/0178066 A1 | 11/2002 | Roh | |
| 2003/0019165 A1 | 1/2003 | Gallant et al. | |
| 2003/0139176 A1 | 7/2003 | Fujiwara et al. | |
| 2003/0172072 A1 | 9/2003 | Smith | |
| 2003/0189429 A1 | 10/2003 | Belenger et al. | |
| 2004/0034581 A1 | 2/2004 | Hill et al. | |
| 2004/0130331 A1 | 7/2004 | Frederick et al. | |
| 2005/0060242 A1 | 3/2005 | Armstrong et al. | |
| 2005/0075954 A1 | 4/2005 | Matsumoto et al. | |
| 2005/0187744 A1* | 8/2005 | Morrison | G06Q 10/06 |
| | | | 703/2 |
| 2006/0053075 A1 | 3/2006 | Roth et al. | |
| 2006/0155595 A1 | 7/2006 | Johannsen | |
| 2007/0013489 A1 | 1/2007 | Bechtle et al. | |
| 2008/0025734 A1 | 1/2008 | Kehoe et al. | |
| 2008/0291015 A1 | 11/2008 | Charles | |
| 2009/0030749 A1 | 1/2009 | Drummond et al. | |
| 2009/0204512 A1 | 8/2009 | Connell, II et al. | |
| 2009/0212927 A1 | 8/2009 | Flick | |
| 2010/0106626 A1 | 4/2010 | Ashrafzadeh et al. | |
| 2011/0099507 A1 | 4/2011 | Nesladek et al. | |
| 2012/0022965 A1 | 1/2012 | Seergy | |
| 2012/0154169 A1 | 6/2012 | Hoekstra | |
| 2012/0271645 A1 | 10/2012 | Dain et al. | |
| 2013/0117053 A2 | 5/2013 | Campbell | |
| 2013/0201018 A1 | 8/2013 | Horstemeyer et al. | |
| 2014/0006131 A1* | 1/2014 | Causey | G06Q 30/0251 |
| | | | 705/14.24 |
| 2014/0084060 A1 | 3/2014 | Jain et al. | |
| 2014/0089088 A1 | 3/2014 | Umeda | |
| 2014/0203915 A1 | 7/2014 | Puleston et al. | |
| 2014/0207619 A1 | 7/2014 | Ishebabi | |
| 2014/0278735 A1 | 9/2014 | Gettings et al. | |
| 2014/0283144 A1* | 9/2014 | Gettings | G08B 23/00 |
| | | | 726/30 |
| 2014/0297487 A1 | 10/2014 | Bashkin | |
| 2015/0052978 A1* | 2/2015 | Beier | B01D 46/0086 |
| | | | 73/38 |
| 2015/0149298 A1 | 5/2015 | Tapley | |
| 2015/0178654 A1 | 6/2015 | Glasgow et al. | |
| 2015/0185751 A1 | 7/2015 | Karc et al. | |
| 2015/0302510 A1* | 10/2015 | Godsey | G06Q 30/0635 |
| | | | 705/26.81 |
| 2015/0338281 A1 | 11/2015 | Ross et al. | |
| 2016/0132821 A1 | 5/2016 | Glasgow et al. | |
| 2019/0064800 A1 | 2/2019 | Frazzoli et al. | |
| 2019/0064801 A1 | 2/2019 | Frazzoli et al. | |
| 2019/0064802 A1 | 2/2019 | Frazzoli et al. | |
| 2019/0064803 A1 | 2/2019 | Frazzoli et al. | |
| 2019/0064804 A1 | 2/2019 | Frazzoli et al. | |
| 2019/0064805 A1 | 2/2019 | Frazzoli et al. | |
| 2019/0087769 A9 | 3/2019 | Glasgow et al. | |
| 2020/0034912 A1 | 1/2020 | Glasgow et al. | |
| 2021/0016781 A1 | 1/2021 | Karunai-Ramanujam et al. | |
| 2021/0248549 A1 | 8/2021 | Glasgow et al. | |
| 2021/0279665 A1 | 9/2021 | Glasgow et al. | |
| 2023/0410042 A1 | 12/2023 | Glasgow et al. | |

FOREIGN PATENT DOCUMENTS

| | | |
|---|---|---|
| CA | 2934326 | 4/2019 |
| CN | 101067860 | 11/2007 |
| CN | 102905113 | 1/2013 |
| CN | 105981059 | 9/2016 |
| JP | 2003185327 A | 7/2003 |
| KR | 1020000063201 | 11/2000 |
| KR | 1020030015411 | 2/2003 |
| KR | 20090003488 | 1/2009 |
| KR | 1020090003488 | 1/2009 |
| WO | 2015077637 | 5/2015 |
| WO | 2015095493 | 6/2015 |

OTHER PUBLICATIONS

"International Application Serial No. PCT US2014 071103, Invitation to Pay Additional Fees and Partial Search Report mailed Mar. 19, 2015", 2 pgs.

"International Application Serial No. PCT US2014 071103, International Search Report mailed May 21, 2015", 4 pgs.

"International Application Serial No. PCT US2014 071103, Written Opinion mailed May 21, 2015", 7 pgs.

"International Application Serial No. PCT US2014 071103, International Preliminary Report on Patentability mailed Jun. 30, 2016", 9 pgs.

"U.S. Appl. No. 14/538,696, First Action Interview-Pre-Interview Communication mailed Sep. 21, 2016", 4 pgs.

"U.S. Appl. No. 14/538,696, First Action Interview—Office Action Summary mailed Dec. 21, 2016", 6 pgs.

"Australian Application Serial No. 2014364486, First Examiners Report mailed Dec. 23, 2016", 5 pgs.

"Korean Application Serial No. 2016-7019607, Office Action mailed Feb. 24, 2017", with English Translation, 7 pgs.

"Canadian Application Serial No. 2,934,326, Office Action mailed May 1, 2017", 5 pgs.

"U.S. Appl. No. 14/538,696, Final Office Action mailed May 15, 2017", 29 pgs.

"U.S. Appl. No. 14/569,188, Non Final Office Action mailed May 16, 2017", 17 pgs.

"U.S. Appl. No. 14/569,188, Examiner Interview Summary mailed Aug. 2, 2017", 3 pgs.

"Korean Application Serial No. 2016-7019607, Office Action mailed Aug. 23, 2017", w English Claims, 5 pgs.

"U.S. Appl. No. 14/569,188, Final Office Action mailed Sep. 8, 2017", 22 pgs.

(56) References Cited

OTHER PUBLICATIONS

"U.S. Appl. No. 14/538,696, Non Final Office Action mailed Oct. 30, 2017", 30 pgs.
"U.S. Appl. No. 14/569,188, Advisory Action mailed Dec. 4, 2017", 3 pgs.
"Korean Application Serial No. 2016-7019607, Final Office Action mailed Feb. 27, 2018", w English Translation, 9 pgs.
"U.S. Appl. No. 14/569,188, Non Final Office Action mailed Mar. 20, 2018", 26 pgs.
"U.S. Appl. No. 14/538,696, Final Office Action mailed Apr. 6, 2018", 15 pgs.
"Canadian Application Serial No. 2,934,326, Office Action mailed Apr. 5, 2018", 5 pgs.
"Korean Application Serial No. 2016-7019607, Notice of Dismissal of Amendment and Notice of second Final Rejection (Second Final) mailed May 15, 2018", w English Translation, 7 pages.
"Australian Application Serial No. 2017219097, First Examination Report mailed Jun. 24, 2018", 3 pgs.
"Decision on Pre-Appeal Brief received for U.S. Appl. No. 14/538,696, mailed on Jul. 19, 2018", (Jul. 19, 2018), 2 pages.
"Pre-Appeal Brief for U.S. Appl. No. 14/538,696, filed on Jun. 25, 2018", (Jun. 25, 2018), 5 pages.
"U.S. Appl. No. 14/569,188, Final Office Action mailed Aug. 15, 2018", 28 pgs.
"U.S. Appl. No. 14/538,696, Appeal Brief filed Sep. 25, 2018", 19 pgs.
"U.S. Appl. No. 14/569,188, Examiner Interview Summary mailed Nov. 7, 2018", 3 pgs.
"U.S. Appl. No. 14/569,188, Non Final Office Action mailed Dec. 19, 2018", 30 pgs.
"Chinese Application Serial No. 201480075184.6, Office Action mailed Jan. 2, 2019", With English translation, 19 pgs.
"Australian Application Serial No. 2017219097, Subsequent Examiners Report mailed Jan. 15, 2019", 4 pgs.
"U.S. Appl. No. 14/569,188, Non Final Office Action mailed May 6, 2019", 31 pgs.
"U.S. Appl. No. 14/569,188, Examiner Interview Summary mailed Jun. 19, 2019", 3 pgs.
"Australian Application Serial No. 2017219097, Subsequent Examiners Report mailed Jun. 21, 2019", 4 pgs.
"Chinese Application Serial No. 201480075184.6, Office Action mailed Jul. 25, 2019", With English machine translation, 24 pgs.
"U.S. Appl. No. 14/569,188, Final Office Action mailed Sep. 26, 2019", 32 pgs.
"Chinese Application Serial No. 201480075184.6, Decision of Rejection mailed Nov. 5, 2019", With English translation, 12 pages (7 pages official copy and 5 pages English translation).pgs.
"U.S. Appl. No. 14/569,188, Non Final Office Action mailed Jan. 27, 2020", 34 pgs.
"Korean Application Serial No. 2018-7020143, Notice of Preliminary Rejection mailed Mar. 3, 2020", With English machine translation, 16 pgs.
"Australian Application Serial No. 2019204416, First Examination Report mailed Apr. 1, 2020", 3 pgs.
"U.S. Appl. No. 14/569,188, Final Office Action mailed Jul. 15, 2020", 38 pgs.
"U.S. Appl. No. 14/538,696, Appeal Decision mailed Jul. 17, 2020", 15 pgs.
"U.S. Appl. No. 14/538,696, Examiner Interview Summary mailed Dec. 16, 2020", 3 pgs.
"U.S. Appl. No. 17/241,137, Examiner Interview Summary mailed Dec. 5, 2022", 2 pgs.
"U.S. Appl. No. 17/328,206, Final Office Action mailed Dec. 20, 2022", 22 pgs.
"U.S. Appl. No. 17/241,137, Final Office Action mailed Feb. 9, 2023", 20 pgs.
"U.S. Appl. No. 17/328,206, Examiner Interview Summary mailed Feb. 9, 2023", 2 pgs.
"U.S. Appl. No. 14/538,696, Corrected Notice of Allowability mailed Apr. 27, 2021", 2 pgs.
"U.S. Appl. No. 14/538,696, Corrected Notice of Allowability mailed May 6, 2021", 2 pgs.
"U.S. Appl. No. 14/538,696, Non Final Office Action mailed Sep. 24, 2020", 23 pgs.
"U.S. Appl. No. 14/538,696, Notice of Allowance mailed Feb. 1, 2021", 9 pgs.
"U.S. Appl. No. 14/569,188, Advisory Action mailed Oct. 19, 2020", 3 pgs.
"U.S. Appl. No. 14/569,188, Examiner Interview Summary mailed Sep. 17, 2020", 3 pgs.
"U.S. Appl. No. 14/569,188, Notice of Allowance mailed Apr. 21, 2021", 16 pgs.
"U.S. Appl. No. 14/588,320, Advisory Action mailed Jun. 7, 2018", 6 pgs.
"U.S. Appl. No. 14/588,320, Examiner Interview Summary mailed Mar. 1, 2019", 4 pgs.
"U.S. Appl. No. 14/588,320, Examiner Interview Summary mailed May 4, 2018", 3 pgs.
"U.S. Appl. No. 14/588,320, Examiner Interview Summary mailed Oct. 25, 2018", 3 pgs.
"U.S. Appl. No. 14/588,320, Examiner Interview Summary mailed Dec. 15, 2017", 3 pgs.
"U.S. Appl. No. 14/588,320, Final Office Action mailed Mar. 2, 2018", 27 pgs.
"U.S. Appl. No. 14/588,320, Final Office Action mailed Dec. 17, 2018", 34 pgs.
"U.S. Appl. No. 14/588,320, Non Final Office Action mailed Aug. 7, 2018", 42 pgs.
"U.S. Appl. No. 14/588,320, Non Final Office Action mailed Aug. 30, 2017", 22 pgs.
"U.S. Appl. No. 14/588,320, Notice of Allowance mailed Jun. 5, 2019", 16 pgs.
"U.S. Appl. No. 16/590,362, Examiner Interview Summary mailed Jun. 3, 2022", 2 pgs.
"U.S. Appl. No. 16/590,362, Examiner Interview Summary mailed Aug. 3, 2021", 3 pgs.
"U.S. Appl. No. 16/590,362, Examiner Interview Summary mailed Oct. 13, 2021", 3 pgs.
"U.S. Appl. No. 16/590,362, Final Office Action mailed Aug. 20, 2021", 31 pgs.
"U.S. Appl. No. 16/590,362, Non Final Office Action mailed Mar. 10, 2022", 12 pgs.
"U.S. Appl. No. 16/590,362, Non Final Office Action mailed May 10, 2021", 36 pg.
"U.S. Appl. No. 16/590,362, Notice of Allowance mailed Aug. 17, 2022", 9 pgs.
"U.S. Appl. No. 16/590,362, Supplemental Notice of Allowability mailed Oct. 3, 2022", 3 pgs.
"U.S. Appl. No. 16/590,362, Supplemental Notice of Allowability mailed Dec. 15, 2022", 2 pgs.
"U.S. Appl. No. 17/328,206, Non Final Office Action mailed Jul. 27, 2022", 19 pgs.
"Australian Application Serial No. 2019204416, Subsequent Examiners Report mailed Mar. 26, 2021", 5 pgs.
"Australian Application Serial No. 2019204416, Subsequent Examiners Report mailed Sep. 30, 2020", 5 pgs.
"Australian Application Serial No. 2019204416, Subsequent Examiners Report mailed Dec. 9, 2020", 5 pgs.
"Chinese Application Serial No. 201480075184.6, Notice of Reexamination mailed Jul. 15, 2021", With English machine translation, 12 pages.
"Korean Application Serial No. 10-2021-7033544, Final Office Action mailed Jun. 24, 2022", w/ English translation, 6 pgs.
"Korean Application Serial No. 10-2021-7033544, Notice of Preliminary Rejection mailed Jan. 4, 2022", w/ English translation, 13 pgs.
"Korean Application Serial No. 2018-7020143, Final Office Action mailed Apr. 20, 2021", 3 pgs.
"Korean Application Serial No. 2018-7020143, Notice of Final Decision of Rejection mailed Jul. 16, 2021", w/ English Translation, 8 pgs.

(56) References Cited

OTHER PUBLICATIONS

"Korean Application Serial No. 2018-7020143, Notice of Preliminary Rejection mailed Oct. 23, 2020", w/ English translation, 10 pgs.

Gannon, Mary C, "Penton Media, Inc., Penton Business Media, Inc. and their subsidiaries", Hydraulics & Pneumatics63.8: 46(5), (Aug. 1, 2010), 4 pgs.

Hsu, C F, "Smart Pantries for Homes", IEEE International Conference on Systems, Man, and Cybernetics vol. 5, (2006), 4276-4283.

Humphries, Matthew, "Panasonic Introduces Auto-Adjusting Energy-Saving Lighting", Geek Newsletter, [Online] Retrieved from the internet: Geek.com <http://www.geek.com/gadgets/panasonic-introduces-auto-adjusting-energy-saving-lighting-683101/>, (Feb. 2, 2009), 2 pgs.

Lee, Loo Hay, et al., "The Impacts of an Electronic Marketplace with Multiple Independent Retailers for Smart Grocery Ordering Systems", Wireless Personal Communications, 60(3), Springer Science Business Media, LLC, (Apr. 9, 2011), 475-487.

Lin, Chin-Tsai, et al., "An ERP model for supplier selection in electronics industry", Expert Systems with Applications 38, Elsevier, (2011), 1760-1765.

Louella, Fernandes, "Internet of Things: A New Era for Smart Printing?", <https://www.louellafernandes.com/2014/04/22/internet-things-new-era-smart-printing/>, (2014).

Merriam, Webster, "definition: electromechanical", <https://web.archive.Org/web/20090425173005/https://www.merriam-webster.com/dictionary/electromechanical>, (2009).

Wang, Shu-Jen, et al., "The simulated impact of RFID-enabled supply chain on pull-based inventory replenishment in TFT-LCD industry", International Journal of Production Economics, 112(2), Elsevier, (Feb. 28, 2006), 270-586.

"U.S. Appl. No. 17/241,137, Examiner Interview Summary mailed Apr. 7, 2023", 3 pgs.

"U.S. Appl. No. 17/328,206, Non Final Office Action mailed May 11, 2023", 12 pgs.

"U.S. Appl. No. 17/241,137, Notice of Allowance mailed May 15, 2023", 19 pgs.

"U.S. Appl. No. 17/328,206, Examiner Interview Summary mailed Jun. 30, 2023", 2 pgs.

"U.S. Appl. No. 17/328,206, Notice of Allowance mailed Aug. 22, 2023", 18 pgs.

"U.S. Appl. No. 17/241,137, Notice of Allowance mailed Sep. 1, 2023", 10 pgs.

"U.S. Appl. No. 17/241,137, Corrected Notice of Allowability mailed Sep. 20, 2023", 2 pgs.

"U.S. Appl. No. 17/328,206, Corrected Notice of Allowability mailed Nov. 17, 2023", 2 pgs.

U.S. Appl. No. 18/388,215, filed Nov. 9, 2023, Managed Inventory.

\* cited by examiner

100

300

400

550

500

600

METHOD, NON-TRANSITORY COMPUTER-READABLE MEDIA, AND SYSTEM FOR E-COMMERCE REPLACEMENT OR REPLENISHMENT OF CONSUMABLE

CROSS-REFERENCE TO RELATED APPLICATIONS

This application is a continuation of U.S. patent application Ser. No. 16/590,362, filed Oct. 1, 2019, which is a continuation of U.S. patent application Ser. No. 14/588,320, filed on Dec. 31, 2014, now U.S. Pat. No. 10,430,858, issued on Oct. 1, 2019; the disclosure of which is incorporated herein by reference in its entirety.

FIELD OF THE INVENTION

The present disclosure relates to a method and system for replacing or replenishing a consumable. More specifically, it relates to an order satisfaction system responding to an indication of imminent failure or depletion of a consumable based on detected parameters.

BACKGROUND

Consumables are goods that are used, depleted, spent, dissipated, wasted, or the like. Some consumables are replaced, e.g., with a refill or a replacement. Consumables may include office supplies such as computer toner, paper, and pens; household supplies such as water filters, toilet paper, soap, and light bulbs; and other types of refillable or replaceable items in other contexts or environments. For some consumables, it is difficult to predict when the consumable will require refill or replacement. For these types of consumables, accompanying challenges include when to purchase a replacement for the consumable and, where alternatives are available, what to purchase and or use as a replacement.

DETAILED DESCRIPTION

In an embodiment, a method for replacing a consumable includes automatically receiving data regarding a state of a consumable. Based on the state of the consumable, the method may determine that a performance of the consumable is below a threshold. If the performance of the consumable is below the threshold, the method may identify a replacement for the consumable. The method may automatically place an order for the replacement.

Some embodiments determine when to replace a consumable. For example, a consumable may be replaced at a definable period before partial or total failure. As another example, a consumable may be replaced "just in time." In some embodiments, the timing of the replacement may prevent overpurchase or underpurchase. Some embodiments may identify and/or offer an alternative replacement. For example, a method may recommend an alternative refill or replacement that performs similarly to a current refill or replacement for a consumable. As another example, a method may recommend an alternative replacement that performs better than a current refill or replacement for a consumable. The method may recommend an alternative refill based on simulations while avoiding trial and error. In the context of the present disclosure, performance may include not only physical characteristics, but also price and availability.

Figure 1:
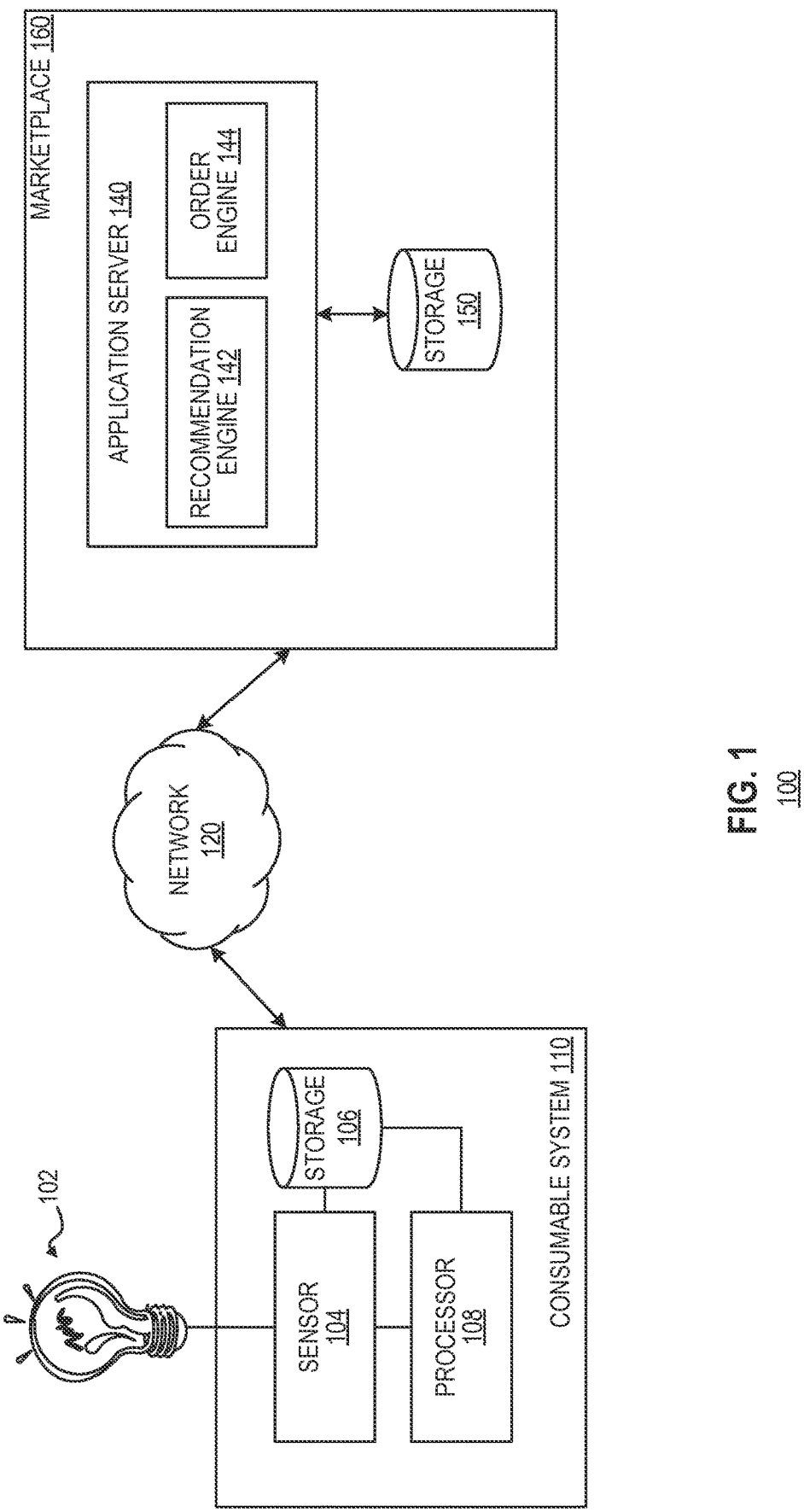
FIG. 1 is a simplified block diagram of a system according to an embodiment.

FIG. 1 is a simplified block diagram of a system 100 implementing the methods and systems described herein. The system 100 may include marketplace 160 and a consumable system 110. Each element of the system 100 may exchange data via a network 120 such as the Internet. The marketplace 160 may publish content gathered, generated, or derived from the elements of the system. The consumable system 110 may provide data to and receive data from the marketplace 160.

The consumable system 110 may include a sensor 104, a processor 108, and in some instances storage 106. In an embodiment, the consumable system 110 may be communicatively coupled to a consumable 102. In an alternative embodiment, the consumable system 110 may include the consumable 102. In another embodiment, the consumable system may include just processor 108 and apparatus to communicate with the network 120. Sensor 104 may be separate from the rest of consumable system 110. For illustrative, non-limiting purposes, purely by way of example, the consumable is represented as a light bulb.

The sensor 104 may be coupled to the consumable 102 and may be an on-body or off-body sensor. The sensor 104 may detect a behavior of the consumable. The sensor 104 may detect characteristics of a setting in which the consumable is used. An on-body sensor may be placed on or in the vicinity of the consumable to measure performance of the sensor. For example, an on-body sensor for a refrigerator may be a camera placed on the refrigerator. As another example, an on-body sensor for a light bulb may be a sensor to sense an electrical characteristic of the light bulb such as a resistance of the filament. An off-body sensor may be placed in the vicinity of the consumable or within an area in which the effects of the consumable may be measured. For example, an off-body sensor for a light bulb may be a sensor placed on a switch for the light bulb to detect a characteristic provided by the light bulb. For example, the characteristic may include a brightness or a temperature of the light bulb. As another example, an off-body sensor may be a sensor plugged into an electrical outlet in a room to sense conditions in the room caused by the light bulb. These conditions may include a brightness of the room and a warmth of the room.

The processor 108 may process sensor readings collected by the sensor 104. For example, the processor 108 may analyze data detected by sensor 104. In an embodiment, the processor 108 may determine operating conditions of the consumable 102 such as an efficiency of the consumable. In an embodiment, the processor may monitor characteristics of the consumable 102. For example, the processor may monitor a usage characteristic or an efficiency of the consumable. This information may be used to generate a recommendation of an alternative replacement with comparable characteristics. Sensor readings may be stored in storage 106, or may be communicated directly over network 120. In an embodiment, the sensor readings may be monitored, and communicated over network 120 only when the readings correlate to a need for replacement of the consumable.

Storage 106 may store data related to the consumable such as the specifications of the consumable. In an embodiment, storage 106 may be coupled to the sensor 104 to store sensor readings. In another embodiment, storage 106 may be coupled to the processor 108 to store processor sensor readings. Using a light bulb as an example of a consumable, storage 106 may store a type and/or size of light bulb. This may facilitate backwards and forwards compatibility by allowing the system to analyze several types of light bulbs, including those bulbs developed before or after the light bulb being used.

In operation, the sensor 104 may detect a behavior of the consumable 102 or a setting in which the consumable 102 is used. The detected data may be stored in storage 106. In an embodiment, the consumable system 110 may periodically provide the stored data to the marketplace 160 via the network 120. In an alternative embodiment, the consumable system 110 may provide sensor data directly to the marketplace 160 via the network 120 without first storing the data in storage 106. In yet another embodiment, upon a request, the consumable system 110 may provide data to the marketplace 160.

The marketplace 160 may include an application server 140 and a storage system 150. The marketplace 160 may include a data exchange platform. The data exchange platform may host transactions such as purchasing and selling goods and services including auctions. The data exchange platform may also host processes assisting the transactions such as generating recommendations, synchronizing financial journals, distribution of goods, collection, and payment.

The application server 140 may include a recommendation engine 142 and an order engine 144. The application server 140 may be communicatively coupled to a storage system 150. Each of the recommendation engine 142 and the order engine 144 may be operated according to the methods described herein. For example, the recommendation engine 142 may perform the methods shown in FIGS. 5A and 5B, and the order engine 144 may perform the methods shown in FIG. 6.

The network 120 may include any wired connection, wireless connection, or combination thereof, a non-exhaustive list including: LAN (local area network), WAN (wide area network), VPN (virtual private network), cellular network, satellite network, Wi-Fi network, optical network, the Internet, and a Cloud network. The network 120 may use any combination of transmission protocols or techniques.

Each of the storage systems 106, 150 may include any permanent memory circuit, temporary memory circuit, or combination thereof, a non-exhaustive list including: ROM (read-only memory), RAM (random access memory), EEPROM (electrically erasable programmable read-only memory), Flash memory, CD (compact disk), DVD (digital versatile disk), and hard disk drive.

The system 100 is an illustrative system having a client-server architecture, where the consumable system 110 is a client. The system may be embodied in other types of architectures, including, but not limited to peer-to-peer network environments and distributed network environments.

Figure 2:
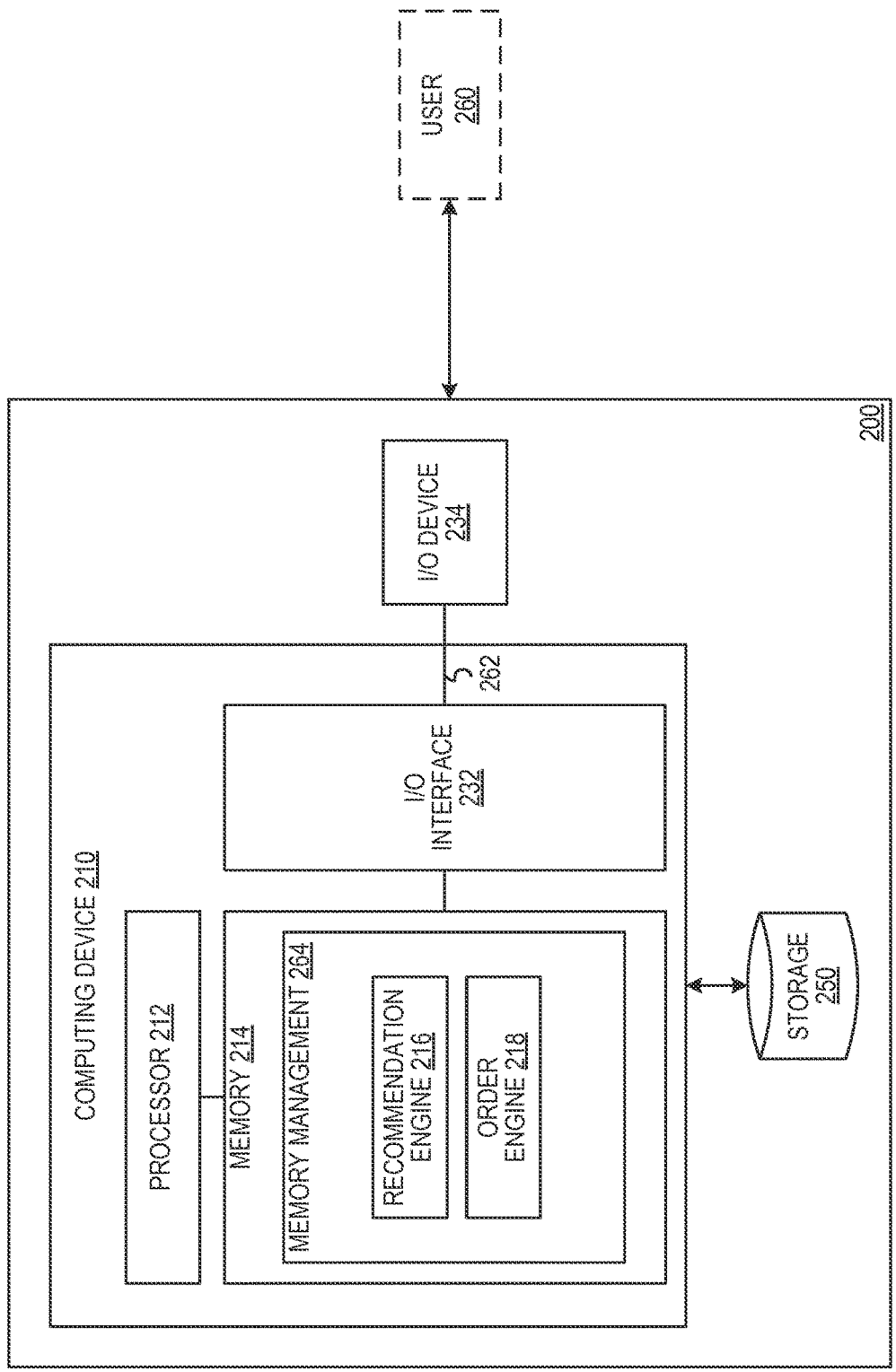
FIG. 2 is a simplified block diagram of a device according to an embodiment.

FIG. 2 is a simplified block diagram of a device 200 for implementing the methods and systems described herein. The device may be a server system or a client system. For example, the application server 140 shown in FIG. 1 may be implemented by the device 200. The device 200 may include a computing device 210, an I/O (input/output) device 234, and a storage system 250. The computing device may include a processor 212, a memory 214, and an I/O interface 232. Each of the components may be connected via a bus 262.

The processor 212 executes computer program code, for example code stored in memory 214 or storage 250. The execution of the code may include reading and/or writing to/from memory 214, storage 250, and/or I/O device 234. The program code may execute the methods described herein.

The memory 214 may include, or may work in conjunction with memory management 264. The memory management may include a recommendation engine 216 and an order engine 218. The recommendation engine 216 may be configured to make computing device 210 operable to recommend a replacement for a consumable. The recommendation engine 216 may implement the methods described herein, e.g., in relation to FIGS. 5A and 5B. The order engine 218 may be configured to make computing device 210 operable to place an order or a replacement for a consumable. The order engine 218 may implement the methods described herein, e.g., in relation to FIG. 6.

One of ordinary skill in the art would understand that recommendation engine 216 and/or order engine 218 need not be part of memory management system 264, but instead may be separate modules or elements. One of ordinary skill in the art also would understand that a different number of engines than the ones shown may be included in memory 214 (or provided separately). The functionality described for each engine may also be apportioned to different engines. Additional engines are also possible. For example, a billing engine may be configured to charge a vendor for at least some of the information stored in storage 250 or memory 214. The billing engine may be further configured to charge vendors for recommending a replacement for a consumable and/or to charge consumers for placing an order for a consumable.

The memory 214 may include local memory usable during execution of program code, cache memory temporarily storing program code, and bulk storage. The local memory may include any permanent memory circuit, temporary memory circuit, or combination thereof, a non-exhaustive list including: ROM, RAM, EEPROM, Flash memory, CD, DVD, and hard disk drive.

The I/O device 234 may include any device enabling a user to interact with the computing device 210, including but not limited to a keyboard, pointing device such as a mouse, touchscreen, microphone, speaker system, computer display, and printer.

The computing device 210 may include any special purpose and/or general purpose computing article of manufacture executing computer program code, including, but not limited to, a personal computer, a smart device such as a smartphone or tablet, and a server. The computing device may be a combination of general and/or specific purpose hardware and/or program code.

The device 200 may be embodied as a single server or a cluster of servers including at least two servers communicating over any type of communications link. A communications link may include any wired connection, wireless connection, or combination thereof, a non-exhaustive list including: LAN (local area network), WAN (wide area network), VPN (virtual private network), cellular network, satellite network, Wi-Fi network, optical network, the Internet, and a Cloud network. The communications link may use any combination of transmission protocols or techniques.

Figure 3:
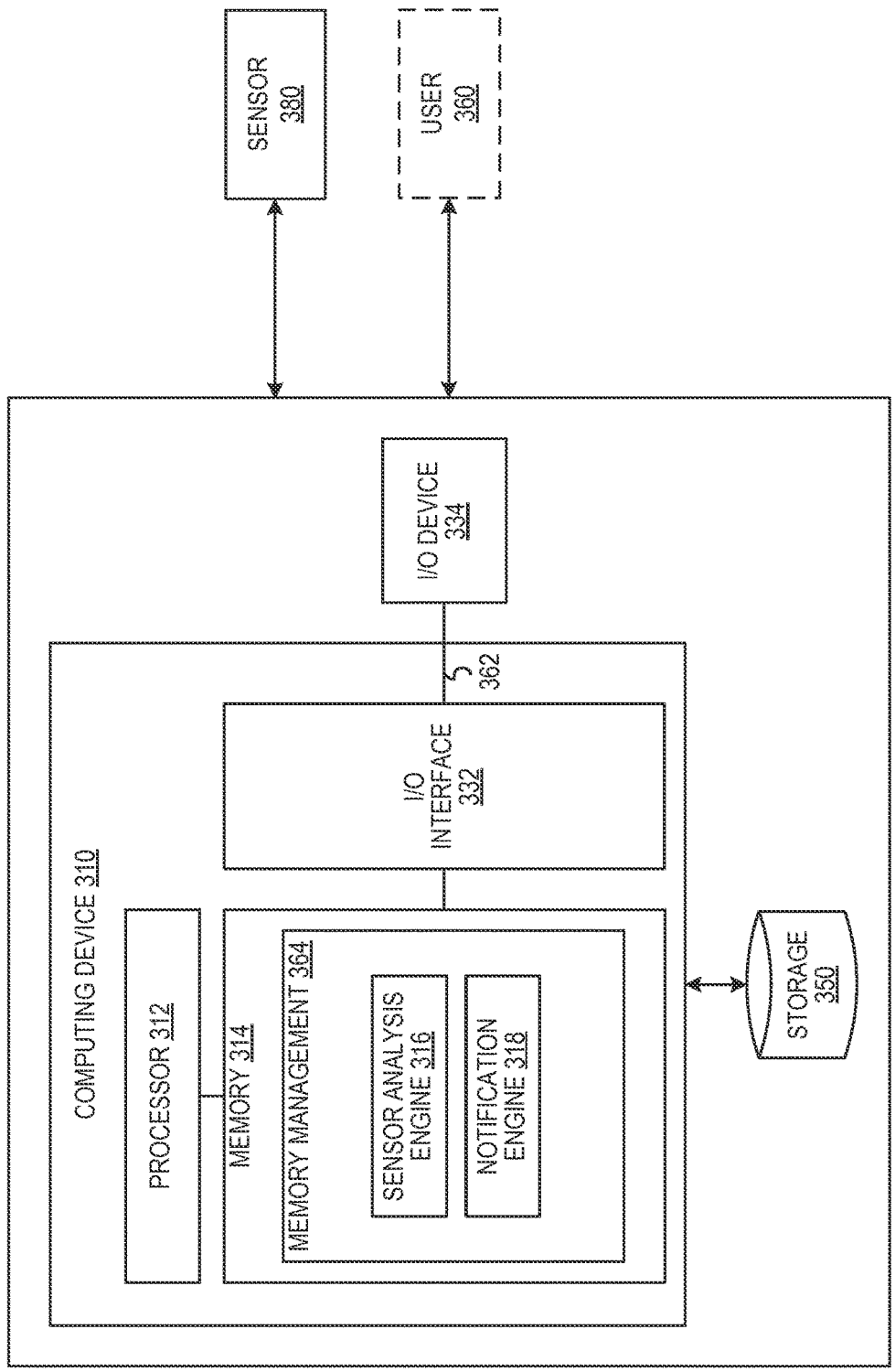
FIG. 3 is a simplified block diagram of a device according to an embodiment.

FIG. 3 is a simplified block diagram of a device 300 for implementing the methods and systems described herein. The device may be a server system or a client system. For example, the processor 108 shown in FIG. 1 may be implemented by the device 300. The device 300 may include a computing device 310, an I/O (input/output) device 334, and a storage system 350. The computing device may include a processor 312, a memory system 314, and an I/O interface 332. Each of the components may be connected via a bus 362.

The processor 312 executes computer program code, for example code stored in memory 314 or storage 350. The execution of the code may include reading and/or writing to/from memory 314, storage 350, I/O device 334, and/or the sensor 380. The program code may execute the methods described herein.

The memory 314 may include, or may work in conjunction with memory management 364. Memory management 364 may include a sensor analysis engine 316 and a notification engine 318. The sensor analysis engine 316 may be configured to make computing device 310 operable to analysis sensor readings, for example readings provided by sensor 380. The sensor analysis engine 316 may implement the methods described herein, e.g., in relation to FIG. 4. The notification engine 318 may be configured to make computing device 310 operable to provide a notification to replace a consumable or to provide a notification of a state of the consumable. The notification engine 318 may implement the methods described herein, e.g., in relation to FIG. 6.

One of ordinary skill in the art would understand that sensor analysis engine 316 and/or notification engine 318 need not be part of memory management system 364, but instead may be separate modules or elements. One of ordinary skill in the art also would understand that a different number of engines than the ones shown may be included in the memory system 314. The functionality described for each engine may also be apportioned to different engines. Additional engines are also possible. For example, a billing engine may be configured to charge a vendor for at least some of the information stored in storage 350 or memory 314. The billing engine may be further configured to charge consumers for providing a notification.

Memory 314 may include local memory usable during execution of program code, cache memory temporarily storing program code, and bulk storage. The local memory may include any permanent memory circuit, temporary memory circuit, or combination thereof, a non-exhaustive list including: ROM, RAM, EEPROM, Flash memory, CD, DVD, and magnetic tape.

The I/O device 334 may include any device enabling a user to interact with the computing device 310, including but not limited to a keyboard, pointing device such as a mouse, touchscreen, microphone, speaker system, computer display, and printer.

The computing device 310 may include any special purpose and/or general purpose computing article of manufacture executing computer program code, including, but not limited to, a personal computer, a smart device such as a smartphone, and a server. The computing device may be a combination of general and/or specific purpose hardware and/or program code.

The device 300 may be embodied as a single server or a cluster of servers including at least two servers communicating over any type of communications link. A communications link may include any wired connection, wireless connection, or combination thereof, a non-exhaustive list including: LAN (local area network), WAN (wide area network), VPN (virtual private network), cellular network, satellite network, Wi-Fi network, optical network, the Internet, and a Cloud network. The communications link may use any combination of transmission protocols or techniques.

Figure 4:
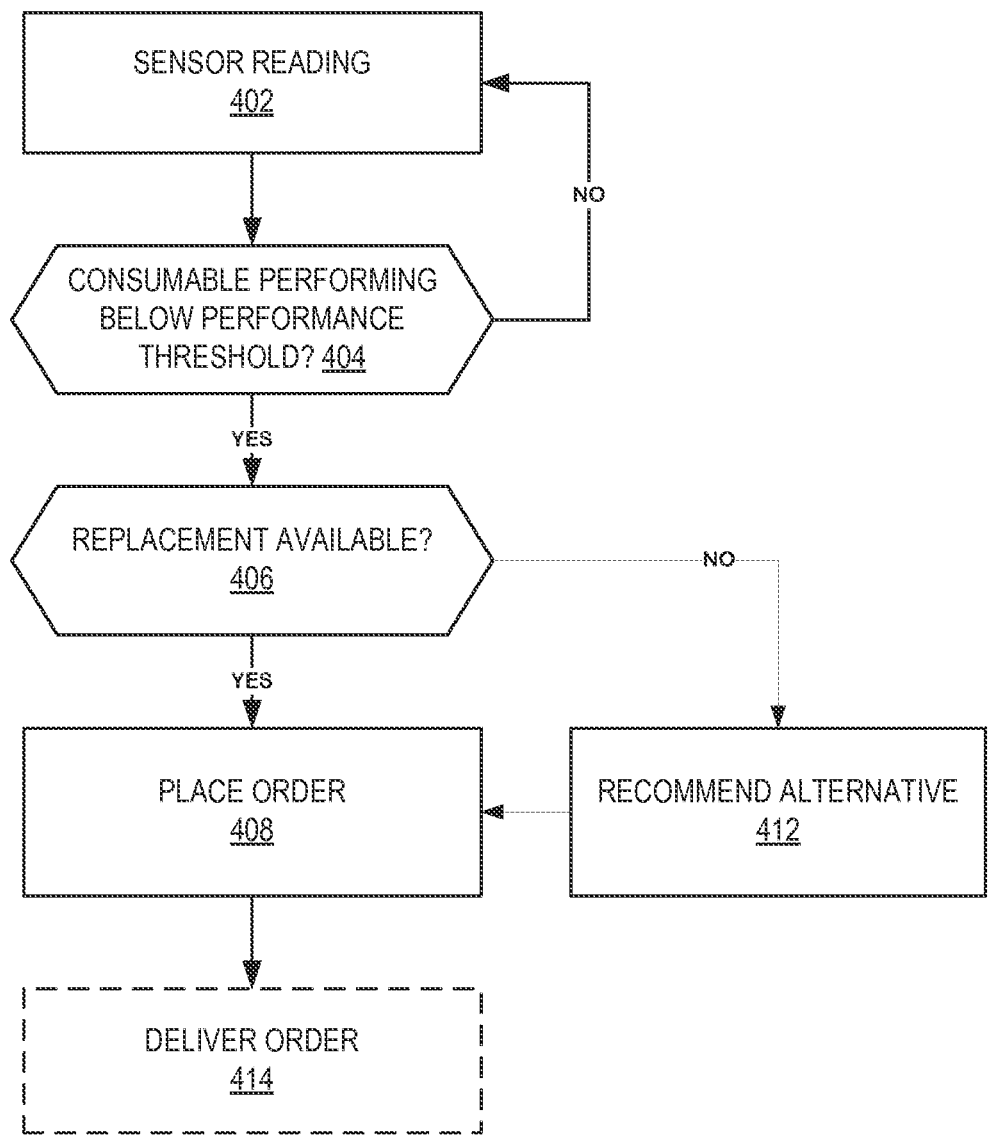
FIG. 4 is a flowchart of a method for replenishing a consumable according to an embodiment.

FIG. 4 is a flowchart of a method 400 for replenishing a consumable. In box 402, the method 400 may receive data from a sensor coupled to the consumable. For example, the data may be detected by sensor 104 shown in FIG. 1 or sensor 380 shown in FIG. 3. The data from the sensor, e.g., a sensor reading, may reflect a state of a consumable. The method 400 may then determine whether the consumable is performing below a threshold (box 404). If the consumable is performing above the threshold level, the method 400 may return to box 402 to obtain another sensor reading. If the consumable is performing below the threshold level, the method 400 may proceed to box 406. In box 406, the method 400 may determine whether a replacement or refill for the consumable is available. If a replacement or refill is available, the method 400 may place an order (box 408). In an embodiment, a replacement or refill will be identical to the consumable.

If a replacement or refill is not available, the method 400 determine whether an alternative may exist, and may recommend the alternative (box 412). The recommendation may be made according to method 500 or method 550 shown in FIGS. 5A and 5B. If the replacement is available, the method proceeds to box 408, in which the method 400 places an order. In an alternative embodiment, even if a replacement is available, the method 400 may provide recommendations for alternative products before placing an order. The recommendation may be made according to methods 500 and 550 shown in FIGS. 5A and 5B.

Figure 6:
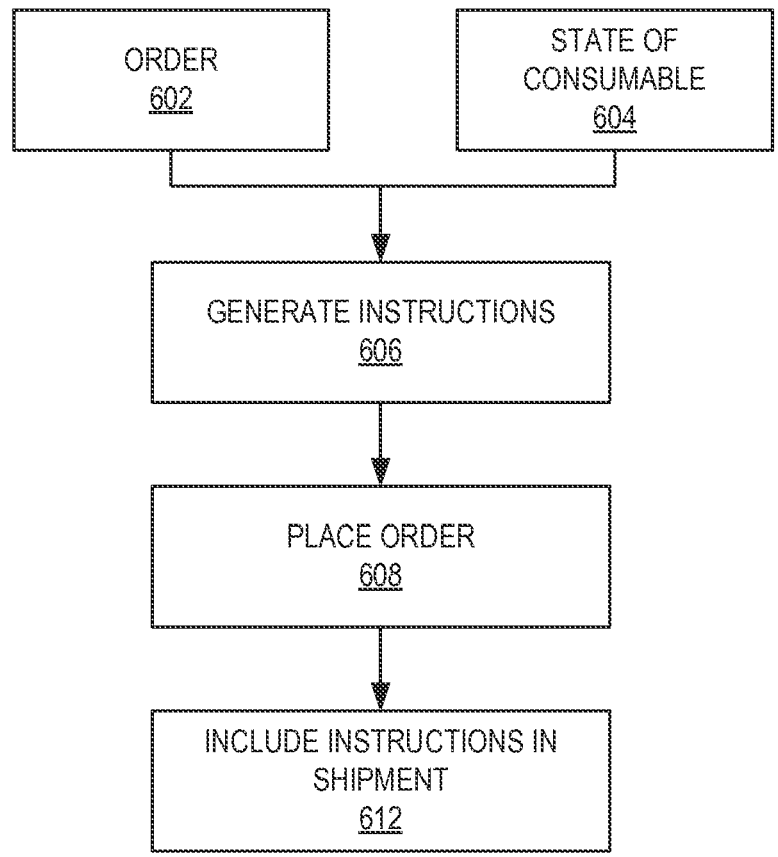
FIG. 6 is a flowchart of a method for placing an order for a consumable according to an embodiment.

In box 408, the order may be placed according to method 600 shown in FIG. 6. Optionally, the method 400 may effect delivery of the order (box 414). For example, the method may notify a third-party merchant, update financial accounts, and/or arrange for delivery of the replacement or refill.

In an embodiment, the sensor reading (box 402) may be performed at periodic intervals. The interval may be predefined. In another embodiment, a sensor reading may be performed responsive to a request. For example, the request may be made by an external device or system such as the marketplace 160 shown in FIG. 1. As another example, the request may be made at the sensor by a user, e.g., via a push of a button.

In an embodiment, the sensor reading (box 402) may be based on an on-body sensor. The on-body sensor may transmit its reading via wireless transmitter, or may be in physical communication with consumable system 110. For example, the wireless transmitter may be implemented as a nano wireless transmitter using Bluetooth® low energy protocol.

In another embodiment, the sensor reading (box 402) may be based on an off-body sensor. The off-body sensor may transmit its reading via wireless transmitter, as noted above, or may be in physical communication with consumable system 110. An off-body sensor may allow for backwards compatibility, by permitting continued use of traditional light bulbs with a replacement.

In an embodiment, a performance threshold (box 404) may be pre-defined. In an alternative embodiment, the method 400 may define a threshold such that the consumable is expected to fail, or to become completely depleted or used up within a time period following the reaching of the threshold. Using the example of a light bulb, the threshold may be an intensity level of brightness and/or warmth below which the light bulb is expected to burn out within two weeks of the light bulb's performance falling below the threshold. In an embodiment, the expected failure or complete consumption of the consumable may be computed or estimated to be some period longer than it would take to place an order for a replacement or refill and complete delivery.

In an embodiment, the determination of whether a replacement or refill is available (box 406) may be based on supplier stock. For example, a replacement or refill may be unavailable if a supplier does not have a replacement or refill in stock or does not expect to have the replacement or refill in stock at the time of expected shipment to a consumer. In another embodiment, the determination of whether a replacement or refill is available includes obtaining specification(s) of the consumable and matching the specification(s) to a database of a marketplace. For example, the specification(s) of the consumable may be obtained from storage 106 shown in FIG. 1, or storage 206 in FIG. 2. Alternatively, the specification(s) of the consumable may be inferred based on sensed characteristics of the consumable. Using a light bulb as an example, the sensed characteristics may be an intensity (e.g., in lumens) or warmth of the light bulb.

Figure 5B:
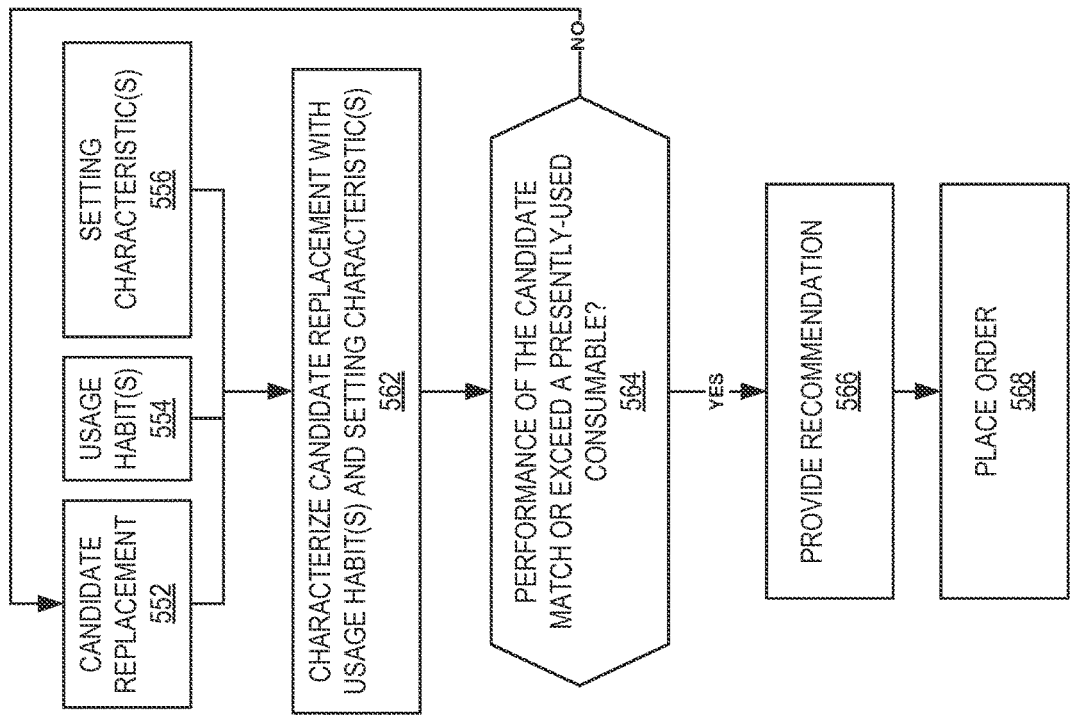
FIG. 5B is a flowchart of a method for recommending an alternative for a consumable according to an embodiment.
Figure 5A:
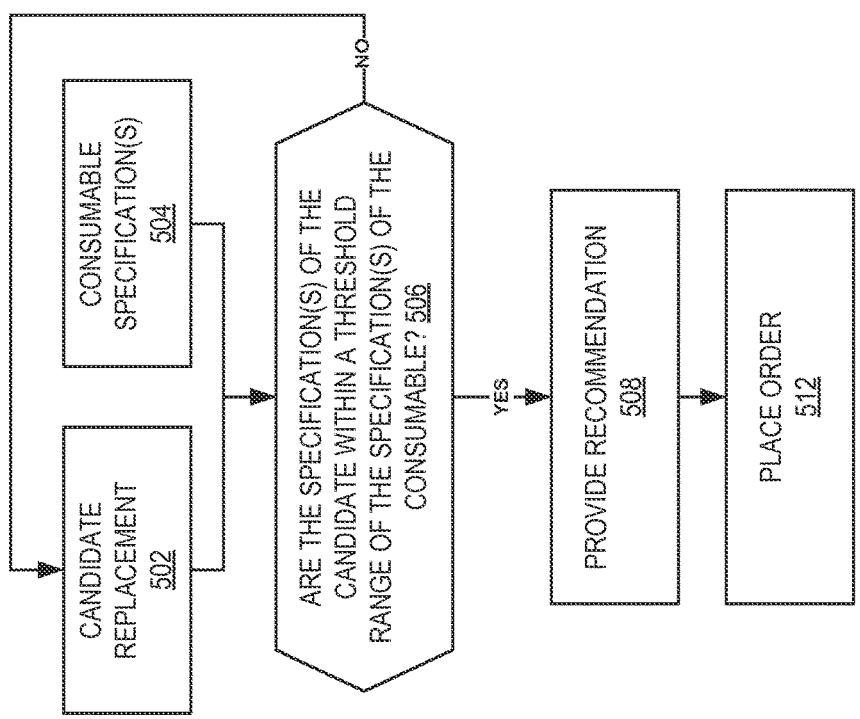
FIG. 5A is a flowchart of a method for recommending an alternative for a consumable according to an embodiment.

FIG. 5A is a flowchart of a method 500 for recommending an alternative for a consumable. The recommendation may be based on one or more characteristics of the consumable. The method 500 may receive a candidate replacement 502 for a consumable and one or more physical, functional, and/or performance specifications for the consumable (box 504). The candidate replacement 502 may be an alternative replacement or refill for the consumable. For example, the candidate replacement may be a different model that provides functionality and/or performance equal or equivalent to that of the currently-used consumable.

At 506, the method 500 may then determine whether the candidate replacement is suitable. In an embodiment, the method 500 may determine that the candidate replacement is suitable if a specification for the candidate replacement is within a range of the received consumable specification (box 504). For instance, a light socket may accommodate bulbs of a particular base size and/or type. A candidate replacement may be considered suitable if it would fit into the light socket. In an embodiment, a candidate replacement may be considered suitable if it provided the same brightness. Price of the candidate replacement also may be a consideration. Where the consumable is a light bulb, the energy consumption of the candidate replacement may be a consideration.

If a specification of the candidate replacement 502 sufficiently matches a specification of the consumable 504, then the method 500 may provide a recommendation for the replacement (box 508). In an embodiment, providing the recommendation (box 508) may include generating a notification including the recommendation for the replacement. The notification may include more than one recommendation. The notification may include an e-mail message to a consumer. In another embodiment, the method 500 may automatically place an order based on the recommendation (box 512). That is, the method 500 may automatically order a replacement for the consumable according to the recommendation.

In box 504, the consumable specifications may include a behavior of a consumable. In an embodiment, the consumable behavior may be a property known at the time of manufacture. In an alternative embodiment, the consumable behavior may be measurable, for example by sensor 104 shown in FIG. 1 or sensor 380 shown in FIG. 3. Where the consumable is a light bulb, specifications for the light bulb may include but are not limited to: intensity, lifespan, and warmth. In an embodiment, the specifications may include energy consumption.

FIG. 5B is a flowchart of a method 550 for recommending an alternative for a consumable. The recommendation may be based on characteristics of a setting in which the consumable is used, and usage habits of a user of the consumable. The method 550 may receive a candidate replacement 552 for a consumable, a usage habit 554, and a setting characteristic 556. In box 562, the method 550 may characterize a candidate replacement based on at least one usage habit 554 and/or at least one setting characteristic 556. The method 550 may then determine whether a performance of the candidate replacement matches or exceeds a presently-used consumable. In an embodiment, performance may be considered substantially matching if at least one performance measure is within a threshold range, below a threshold value, or above a threshold value. In another embodiment, performance of a first consumable may be considered better than performance of a second consumable if the performance of the first consumable is more optimal for a usage habit and/or setting characteristic. For example, a particular light bulb may be used in a particular room for a certain number of hours each day. The method 550 may determine that another type of light bulb may provide substantially the same amount of light and have comparable or better longevity compared with a currently used type of light bulb. In an embodiment, the method 550 may determine that another type of light bulb would use less energy for comparable light emission and/or longevity.

If the method 550 determines that a performance of the candidate replacement 552 is not equal to or better than that a presently-used consumable (box 562), the method may select another candidate replacement 552 for comparison purposes. The process may be repeated until a suitable candidate is found. Alternatively, the process may be repeated a pre-definable number of times, and, if a suitable alternative is not found, the method 550 may place an order for a currently-used type of consumable.

If the method 550 determines that a performance of the candidate replacement is equal to or better than a presently-used consumable, then the method may proceed to box 566, in which the method provides a recommendation to use the replacement. In an embodiment, the providing of the recommendation (box 566) may include generating a notification including the recommendation for the replacement. The notification may include a list of more than one recommendation. The notification may include an e-mail message to a consumer. In another embodiment, the method 550 may automatically place an order based on the recommendation (box 568). That is, the method 550 may automatically order a replacement for the consumable according to the recommendation.

A usage habit 554 may include a characteristic associated with use of a consumable. A usage habit may be unique to a particular consumable, i.e. vary from consumer to consumer based on individual use. In an embodiment, a usage habit may be reported by a user. In an alternative embodiment, a usage habit may be measureable, for example by sensor 104 shown in FIG. 1 or sensor 380 shown in FIG. 3.

For example, usage habits for a light bulb include but are not limited to: length of time the light is on, e.g., number of hours per day, time of day of usage, and/or a purpose for which the light bulb is primarily used, e.g., reading, mood lighting, etc., if information relating to the purpose is available.

A setting characteristic 556 may include a characteristic of a setting in which the consumable is used. The setting characteristic may vary from consumer to consumer. In an embodiment, a setting characteristic may be reported by a user. For example, setting characteristics for a light bulb include but are not limited to: a size of a room in which the light bulb is used, and an average temperature of a room in which the light bulb is used.

In box 562, the method 550 may characterize the candidate replacement with usage habit(s) 554 and/or setting characteristic(s) 556. Using the example of hours of use and an average study room size, the characterization may include determining a longevity of a candidate replacement light bulb and area of brightness to determine how similar the performance of the candidate replacement would be to a presently-used consumable (box 564). In an alternative embodiment, the method 550 may determine that a presently used consumable is not optimal for usage habit(s) and/or setting characteristic(s). Accordingly, the method 550 may quantify a performance measure of a candidate replacement for comparison with a presently-used consumable.

Methods 500 and 550 may be practiced in combination. For example, method 500 may determine that a candidate replacement is suitable for use, and method 550 may select a most efficient replacement from a ranking of all suitable candidate replacements.

In an embodiment, a merchant or other order fulfiller may keep relevant information about particular consumables on hand, including one or more of the performance characteristics discussed above. The method 500 could use some or all of this on-hand information, thereby obviating the need for some or all of the characterization described above.

FIG. 6 is a flowchart of a method 600 for placing an order for a consumable. The placement of the order may be based on expected timing of exhaustion of the consumable. The method 600 may receive an order 602 and a state of a consumable 604. The state of the consumable 604 may include a characteristic of an operating state of the consumable. For example, where the consumable is a light bulb, the characteristic may reflect a state of depletion of the light bulb.

In an embodiment, the method 600 may generate instructions based on the order 602 and the state of the consumable 604 (box 606). The order may be generated according to methods described herein, e.g., methods 500 and 550 shown in FIGS. 5A and 5B. For example, the state of the consumable 604 may indicate that the existing light bulb will burn out in approximately two weeks. The state of the consumable 604 may also indicate that the light bulb is located in a particular room.

In an embodiment, in box 606 the method 600 may generate instructions for when and where to replace the consumable. For example, the instructions may indicate a location of the consumable and an approximate time frame for replacing the consumable. The instructions may be in any form: written, audio, video, etc.

In box 608, the method 600 may order a replacement for a consumable. The method 600 may contact a merchant to place an order. The method 600 may weight factors to determine a supplier from which to order the consumable. Such factors may include, but are not limited to, price, availability, and delivery time. For instance, the method 600 may determine that, according to the state of the consumable 604, a consumable will be usable until two weeks from the present. The method 600 may determine that a first supplier is able to supply the product in 1.5 weeks at a first price, while a second supplier is able to supply the product in one week at a second, higher price than the first price. Based on these determinations, the method 600 may select the first merchant. That is, the method 600 may select a lower-priced supplier who provides the product in a longer time over another supplier who charges more for the product but is able to supply the product more quickly. In box 612, the method 600 may include instructions, which may be based on the instructions optionally generated in box 606, in a shipment to a consumer. This may facilitate the replenishment of the consumable by informing the consumer of an appropriate time and/or place for replacing the consumable.

While the discussion of embodiments herein use a light bulb as an example of a consumable, the embodiments are applicable to other types of consumables, including any consumable whose physical characteristics may be measured and communicated. Another example of such a consumable may be a water filter, whose filter insert may last for a limited time. The method may monitor post-filtration levels, or changes in levels, of one or more contaminants that the filter is supposed to filter out, and may determine from such levels that the filter will cease effective usefulness within a certain period of time. Another example would be printer ink or toner. These last examples of consumables are used in computer printers, some of which have sensors which convey state of use to users. Other similar examples of consumables whose characteristics can be similarly evaluated will be apparent to ordinarily skilled artisans.

Although the disclosure has been described with reference to several exemplary embodiments, it is understood that the words that have been used are words of description and illustration, rather than words of limitation. Changes may be made within the purview of the appended claims, as presently stated and as amended, without departing from the scope and spirit of the disclosure in its aspects. Although the disclosure has been described with reference to particular means, materials and embodiments, the disclosure is not intended to be limited to the particulars disclosed; rather the disclosure extends to all functionally equivalent structures, methods, and uses such as are within the scope of the appended claims.

As used in the appended claims, the term "computer-readable medium" may include a single medium or multiple media, such as a centralized or distributed database, and/or associated caches and servers that store one or more sets of instructions. The term shall also include any medium that is capable of storing, encoding or carrying a set of instructions for execution by a processor or that cause a computer system to perform any one or more of the embodiments disclosed herein.

The computer-readable medium may comprise a non-transitory computer-readable medium or media and/or comprise a transitory computer-readable medium or media. In a particular non-limiting, exemplary embodiment, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. Accordingly, the disclosure is considered to include any computer-readable medium or other equivalents and successor media, in which data or instructions may be stored.

The present specification describes components and functions that may be implemented in particular embodiments which may operate in accordance with one or more particular standards and protocols. However, the disclosure is not limited to such standards and protocols. Such standards are periodically superseded by faster or more efficient equivalents having essentially the same functions. Accordingly, replacement standards and protocols having the same or similar functions are considered equivalents thereof The illustrations of the embodiments described herein are intended to provide a general understanding of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

For example, operation of disclosed embodiments has been described in the context of servers and terminals that embody marketplace and/or product placement systems. These systems can be embodied in electronic devices or integrated circuits, such as application specific integrated circuits, field programmable gate arrays and/or digital signal processors. Alternatively, they can be embodied in computer programs that execute on personal computers, notebook computers, tablets, smartphones or computer servers. Such computer programs typically are stored in physical storage media such as electronic-, magnetic- and/or optically-based storage devices, where they may be read to a processor, under control of an operating system, and executed. And, of course, these components may be provided as hybrid systems that distribute functionality across dedicated hardware components and programmed general-purpose processors, as desired.

In addition, in the foregoing Detailed Description, various features may be grouped or described together for the purpose of streamlining the disclosure. This disclosure is not to be interpreted as reflecting an intention that all such features are required to provide an operable embodiment, nor that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

Also, where certain claims recite methods, sequence of recitation of a particular method in a claim does not require that that sequence is essential to an operable claim. Rather, particular method elements or steps could be executed in different orders without departing from the scope or spirit of the invention.

What is claimed is:

1. A method of replacing a consumable, the method comprising:
filtering a fluid with the consumable disposed at a device;
sensing a volumetric filtration characteristic of the filtered fluid with an on-body sensor disposed at the device, the volumetric filtration characteristic being associated with contaminants in the fluid after filtering the fluid;
comparing the sensed volumetric filtration characteristic with a threshold to determine an effectiveness of the consumable;
receiving sensor settings of an environment within which the device is used by a user of the device from an off-body sensor placed within the environment, the environment being affected by an output of the device and the sensing relating to sensing an effect of the output of the device on the environment;
responsive to the effectiveness of the consumable being below a threshold and the settings of the environment, determining an availability of a first replacement consumable;
receiving user habits relating to use of the consumable by the user of the consumable;
responsive to a determination that the first replacement consumable is unavailable, identifying a second replacement consumable as an alternative to the first replacement consumable based on:
a specification of the consumable;
the user habits relating to the consumable; and
the second replacement consumable exceeding the volumetric filtration specification of the consumable; and
automatically placing an order for the second replacement consumable.

2. The method of claim 1, wherein the user habits are measurable with a sensor and relate to one of a length of time, a time of usage, and a purpose for which the consumable is used.

3. The method of claim 1, wherein the order is placed based on an expected timing of exhaustion of the consumable or a characteristic of an operating state of the consumable.

4. The method of claim 1, wherein the second replacement consumable includes a characteristic upon which the identifying of the second replacement consumable is based, the characteristic selected from the group consisting of: size, capacity, price, availability, and delivery time.

5. The method of claim 1, wherein identifying the second replacement consumable is a result of a determination that the second replacement consumable performs at a level at least equal to a level of performance of the consumable.

6. The method of claim 1, wherein the placing of the order is timed to provide an expected delivery of the second replacement consumable within a pre-definable time period before depletion of the consumable.

7. The method of claim 1, wherein identifying the second replacement consumable is further based on improved performance of the second replacement consumable as compared to the consumable when used in a manner consistent with the user habits.

8. A non-transitory computer-readable media containing instructions, which, in response to being executed by one or more processors, causes a system to perform operation, the operations comprising:
filtering a fluid with a consumable disposed at a device;
sensing a volumetric filtration characteristic of the filtered fluid with an on-body sensor disposed at the device, the volumetric filtration characteristic being associated with contaminants in the fluid after filtering the fluid;

comparing the sensed volumetric filtration characteristic with a threshold to determine an effectiveness of the consumable;

receiving sensor settings of an environment within which the device is used by a user of the device from an off-body sensor placed within the environment, the environment being affected by an output of the device and the sensing relating to sensing an effect of the output of the device on the environment;

responsive to the effectiveness of the consumable being below a threshold and the settings of the environment, determining an availability of a first replacement consumable;

receiving user habits relating to use of the consumable by the user of the consumable;

responsive to a determination that the first replacement consumable is unavailable, identifying a second replacement consumable as an alternative to the first replacement consumable based on:

a specification of the consumable;

the user habits relating to the consumable; and the second replacement consumable exceeding the volumetric filtration specification of the consumable; and automatically placing an order for the second replacement consumable.

9. The non-transitory computer-readable media of claim 8, wherein the user habits are measurable with a sensor and relate to one of a length of time, a time of usage, and a purpose for which the consumable is used.

10. The non-transitory computer-readable media of claim 8, wherein the order is placed based on an expected timing of exhaustion of the consumable or a characteristic of an operating state of the consumable.

11. The non-transitory computer-readable media of claim 8, wherein the second replacement consumable includes a characteristic upon which the identifying of the second replacement consumable is based, the characteristic selected from the group consisting of: size, capacity, price, availability, and delivery time.

12. The non-transitory computer-readable media of claim 8, wherein identifying the second replacement consumable is a result of a determination that the second replacement consumable performs at a level at least equal to a level of performance of the consumable.

13. The non-transitory computer-readable media of claim 8, wherein the placing of the order is timed to provide an expected delivery of the second replacement consumable within a pre-definable time period before depletion of the consumable.

14. The non-transitory computer-readable media of claim 8, wherein identifying the second replacement consumable is further based on improved performance of the second replacement consumable as compared to the consumable when used in a manner consistent with the user habits.

15. A system comprising:

one or more processors; and one or more non-transitory computer-readable media containing instructions, which, in response to being executed by the one or more processors, causes the system to perform operations, the operations comprising:

filtering a fluid with a consumable disposed at a device;

sensing a volumetric filtration characteristic of the filtered fluid with an on-body sensor disposed at the device, the volumetric filtration characteristic being associated with contaminants in the fluid after filtering the fluid;

comparing the sensed volumetric filtration characteristic with a threshold to determine an effectiveness of the consumable;

receiving sensor settings of an environment within which the device is used by a user of the device from an off-body sensor placed within the environment, the environment being affected by an output of the device and the sensing relating to sensing an effect of the output of the device on the environment;

responsive to the effectiveness of the consumable being below a threshold and the settings of the environment, determining an availability of a first replacement consumable;

receiving user habits relating to use of the consumable by the user of the consumable;

responsive to a determination that the first replacement consumable is unavailable, identifying a second replacement consumable as an alternative to the first replacement consumable based on:

a specification of the consumable;

the user habits relating to the consumable; and the second replacement consumable exceeding the volumetric filtration specification of the consumable; and automatically placing an order for the second replacement consumable.

16. The system of claim 15, wherein the user habits are measurable with a sensor and relate to one of a length of time, a time of usage, and a purpose for which the consumable is used.

17. The system of claim 15, wherein the order is placed based on an expected timing of exhaustion of the consumable or a characteristic of an operating state of the consumable.

18. The system of claim 15, wherein the second replacement consumable includes a characteristic upon which the identifying of the second replacement consumable is based, the characteristic selected from the group consisting of: size, capacity, price, availability, and delivery time.

19. The system of claim 15, wherein identifying the second replacement consumable is a result of a determination that the second replacement consumable performs at a level at least equal to a level of performance of the consumable.

20. The system of claim 15, wherein identifying the second replacement consumable is further based on improved performance of the second replacement consumable as compared to the consumable when used in a manner consistent with the user habits and the placing of the order is timed to provide an expected delivery of the second replacement consumable within a pre-definable time period before depletion of the consumable.

* * * * *